United States Patent
Dourdeville

(10) Patent No.: US 6,299,767 B1
(45) Date of Patent: Oct. 9, 2001

(54) HIGH PRESSURE CAPILLARY LIQUID CHROMATOGRAPHY SOLVENT DELIVERY SYSTEM

(75) Inventor: Theodore A. Dourdeville, Marion, MA (US)

(73) Assignee: Waters Investments Limited ( * ) Notice: Subject to any disclaimer, the term of this patent is extended or adjusted under 35 U.S.C. 154(b) by 0 days.

(21) Appl. No.: 09/430,820

(22) Filed: Oct. 29, 1999

(51) Int. Cl.⁷ ................................................. B01D 15/08
(52) U.S. Cl. .................. 210/198.2; 210/656; 210/101; 73/61.56
(58) Field of Search ................................ 210/656, 659, 210/101, 198.2; 73/61.52, 61.56

(56) References Cited

U.S. PATENT DOCUMENTS

| | | | |
|---|---|---|---|
| 4,191,649 | 3/1980 | Hartwick | 210/198.2 |
| 4,233,156 | 11/1980 | Tsukada | 210/101 |
| 4,311,586 | 1/1982 | Baldwin | 210/101 |
| 4,475,821 | 10/1984 | Koch | 366/160 |
| 4,534,659 * | 8/1985 | Dourdeville | 366/338 |
| 4,767,279 | 8/1988 | Dourdeville | 417/18 |
| 4,942,018 | 7/1990 | Munk | 422/70 |
| 4,981,597 | 1/1991 | Allington | 210/656 |
| 4,986,919 | 1/1991 | Allington | 210/656 |
| 4,990,250 | 2/1991 | Hellinger | 210/198.2 |
| 5,094,099 | 3/1992 | Ross | 73/23.37 |
| 5,234,587 | 8/1993 | Allington | 210/198.2 |
| 5,360,320 | 11/1994 | Jameson | 417/4 |
| 5,423,661 | 6/1995 | Gabeler | 417/410.4 |
| 5,531,106 | 7/1996 | Lyon | 73/61.56 |
| 5,637,208 | 6/1997 | Dourdeville | 210/90 |
| 5,638,986 | 6/1997 | Tuominen | 222/1 |
| 5,730,867 | 3/1998 | Drew | 210/198.2 |
| 5,795,469 | 8/1998 | Quinn | 210/198.2 |
| 5,852,231 | 12/1998 | Kaji | 73/61.52 |
| 5,897,781 | 4/1999 | Dourdeville | 210/656 |
| 6,099,724 * | 8/2000 | Dourdeville | 210/198.2 |

OTHER PUBLICATIONS

Christopher D. Bevan and Ian M. Mutton Use of Freeze–Thaw Flow Management for Controlling and Switching Fluid Flow in Capillary Tubes Anal. Chem. 1995, 67, 1470–1473.

M. T. Davis, D. C. Stahl, and T. D. Lee Low Flow High–Performance Liquid Chromatography solvent Delivery System Designed for Tandem Capillary Liquid Chromatography–Mass Spectrometry.

\* cited by examiner

Primary Examiner—Ernest G. Therkorn
(74) Attorney, Agent, or Firm—Brian Michaelis; Anthony J. Janiuk

(57) ABSTRACT

High pressure capillary liquid chromatography solvent delivery is effected at substantially low volume and atmospheric pressure. The low volume solvent composition is subsequently pressurized and expelled at high pressure into a receiving device such as a column. The solvent composition is expelled from a fluid metering system configured to deliver liquids at low pressures to a storage matrix via an isolation valve. The solvent composition is delivered to the storage matrix in reverse order such that the first volume of liquid delivered into the storage matrix is the last volume of liquid expelled out. Liquid pre-existing within the storage matrix is transferred into a fluid accumulator in fluid communication with the storage matrix. The fluid accumulator is enveloped in a pressure caisson which can be pressurized or depressurized in response to sensor signals obtained from a fluid volume displacement transducer and a pressure sensor, in accordance with solvent composition cycle formation. As the caisson is pressurized, the pressure acting on the fluid accumulator causes the solvent composition within the storage matrix to be expelled out past the isolation valve into a chromatographic column.

30 Claims, 4 Drawing Sheets

HIGH PRESSURE CAPILLARY LIQUID CHROMATOGRAPHY SOLVENT DELIVERY SYSTEM

TECHNICAL FIELD

The present invention relates generally to high pressure capillary liquid chromatography, and more particularly to a method and apparatus for high-pressure delivery of solvent or solvent mixtures, such as is useful in the art of liquid chromatography.

BACKGROUND OF THE RELATED ART

The practice of HPLC generally requires that a molecular species to be separated or analyzed be dissolved in a liquid, the mobile phase, and conveyed by that liquid through a stationary phase. In the stationary phase, a large surface area is presented which is in intimate contact with the mobile phase. Mixtures of analyte compounds, dissolved in the mobile phase, can be separated during passage through the column by processes of adsorption or retention, which act differently on the various analyte species. The differential retention causes the analytes to elute from the column with respect to time and volume. The eluting analytes will typically transit through an in-line detector, where quantitative and/or qualitative examination of analytes will occur.

High pressure liquid chromatography (HPLC) solvent delivery systems are used to source either single-component liquids or mixtures of liquids at selected pressures which can range from substantially atmospheric pressure to pressures on the order of ten thousand pounds per square inch. The above pressures are required to force the mobile phase through the fluid passageways of a stationary phase support, where separation of dissolved analytes can occur. The stationary phase support may comprise a packed bed of particles, a membrane or collection of membranes, a microfabricated structure typically comprising an array of fluid passageways etched into a solid support, or an open column or tube.

Often, analysis conditions require the mobile phase composition to change over the course of analysis which is termed "gradient elution". In gradient elution, the viscosity of the mobile phase may change and the pressure necessary to maintain the required volumetric flow rate will change accordingly.

The elution behavior of analyte molecules is a function of the characteristics of both the stationary and mobile phases. To the extent that the properties of the stationary phase may remain substantially fixed throughout the analysis, variation in elution behavior is predominantly a result of variation in the properties of the mobile phase. In an "isocratic mode" of chromatography, the solvent composition remains substantially constant as a function of time, and analytes in the sample will tend to elute when a prescribed mobile phase volume has transited the column. In a "gradient mode" of chromatography, the solvent composition is required to change as a function of time, tracking a user defined profile. In this mode, analytes will elute in response to both the composition and the volume of solvent delivered.

The separation process occurring in liquid chromatography can result in the separation of an injected sample mixture into its component parts. These component parts are eluted from the column in reasonably distinct zones or bands. As these bands pass through a detector, their presence can be monitored and a detector output can be produced. This output includes a pattern of analyte concentration within the eluting bands, which can be represented by means of a time varying electric signal, and gives rise to the nomenclature of a "chromatography peak." These peaks may be characterized with respect to their retention time, that is, the time in which the center of the band transits the detector relative to the time of injection. In many applications, the retention time of a peak is used to infer the identity of the eluting analyte based upon related analyses incorporating standards or calibrants. The retention time of a peak is strongly influenced by the mobile phase composition and by the volume of mobile phase, which has passed over the stationary phase.

The utility of chromatography relies heavily on run-to-run reproducibility, such that a given analysis can be compared with an analysis of standards or calibrants with confidence in the resulting data. Known pumping systems exhibit some non-ideal characteristics which result in diminished separation performance and diminished run-to-run reproducibility.

Among the non-ideal pump characteristics exhibited in known pumping systems are, generally, fluctuations in solvent composition and/or fluctuations in volumetric flow rate. Such volumetric flow rate fluctuations in present and known HPLC pumping systems disadvantageously cause varying retention times for a given analyte. That is, the amount of time that an analyte is retained in the stationary phase fluctuates undesirably as a function of the undesirable volumetric flow rate fluctuations. This creates difficulties in inferring the identity of a sample from the retention behavior of the components. Volumetric flow rate fluctuations can result in fluctuations in solvent composition when the output of multiple pumps is summed to provide a solvent composition.

Fluctuations in solvent composition in present and known HPLC systems disadvantageously result in interactions with the systems analyte detector and produce perturbations which are detected as if they arose from the presence of a sample. In effect, an interfering signal is generated. This interfering signal is summed with the actual signal attributable to the analyte, producing errors when the quantity of an unknown sample is calculated from the area of the eluting sample peak.

In light of the above, the requirements imposed on HPLC solvent delivery systems are severe. HPLC pumps are typically required to deliver solvents at pressures which can range from several pounds per square inch to as much as 10,000 pounds per square inch. There are problems and non-ideal effects associated with delivering liquids for chromatography against elevated pressures including seal deformation under load and absolute seal leakage. HPLC pumps are expected to output the mobile phase solvent at precisely controlled flow rates in a smooth and uniform manner. In the case of gradient chromatography or in the case of isocratic chromatography, where a fixed solvent composition is blended in real time during the separation, there is the further requirement that mobile phase composition as well as flow rate be precisely and accurately controlled during delivery. However, system operating pressures may be changing very substantially during the separation and the compressibilities of the constituent mobile phase solvents may be quite different.

The large errors associated with the compression or relaxation of large volumes of fluid can be minimized by the use of small volume syringe pumps that utilize multiple syringe strokes to deliver solvent through the course of a chromatographic separation period. However, these pumps typically suffer from flow perturbations associated with the transition of fluid delivery from one syringe cycle to the next.

An emerging area of chromatographic separation and analysis is developing around the use of extremely narrow bore separation columns. Such columns have been termed "capillary columns" with diameters typically in the range of 30 to 800 micron internal diameter. Such columns may be packed with a particulate packing material, or in the smallest diametral range, the stationary phase may be provided by the column wall itself or a coating applied to that wall. Mobile phase flow rates for such particulate packed capillary columns can typically range from approximately one nanoliter per minute to ten or more microliters per minute. These figures represent a three to six order-of-magnitude reduction in flow rate and consequently a similar reduction in the volume of the separation from what is currently practiced on, for example, the four millimeter internal diameter columns widely commercially available. HPLC systems designed around capillary columns have particular utility when the HPLC separation is coupled with a downstream process that does not readily tolerate large amounts of HPLC mobile phase, or where the use of unusually expensive mobile phases is desired. Examples of such processes are: (1) mass spectrometry, which requires that the sample reside in the gas phase at high vacuum conditions prior to mass analysis, (2) infrared spectroscopy, where organic solvents used for HPLC must be eliminated because they represent an interference to analyte detection in the infrared region of the electromagnetic spectrum, (3) microfraction collection, which requires that the analyte be deposited in a small volume on a collection substrate with minimum associated background contamination from the HPLC mobile phase, and (4) nuclear magnetic resonance spectroscopy (NMR) which can benefit from significant signal background reduction through the use of somewhat exotic mobile phases, such as deuterium-substituted mobile phases in the case of proton-NMR.

Substantially, the same requirements for precision and accuracy of solvent composition and flow rate delivery exist as for larger scale chromatography, but the mechanisms for controlling delivery must function at approximately one one-thousandth or less of the conventional volume scale. In particular, the non-idealities of a given implementation which could be dismissed at a much larger volumetric scale give rise to overwhelmingly large perturbations to a system of the scale of capillary HPLC.

A known implementation of a continuous-delivery pumping system for normal analytical scale HPLC (1 to 4 mm column ID), available from Hewlett-Packard and selling under the product designation HP1090/DR5, formed a gradient at run time using a plurality of positive-displacement piston pumps operating against a modest intermediate pressure. The summed output was fed to a low-pressure accumulator and then to a serial or in-line booster pump stage constructed on a diaphragm principle. The booster pump operated at a fixed frequency of approximately 10 Hz, but had a variable stroke volume which accommodated the output flow of the solvent metering/proportioning stage. The booster stage would take the proportioned mixture from the intermediate pressure to the full system operating pressure, which was in the conventional (5000 to 6000 PSIG) HPLC range. Because of the series construction employed, the pump had a delay volume of not less than approximately 300 microliters. This delay volume is quite acceptable for 2 mm ID and 4 mm ID column work, but becomes significant at 1 mm ID column size, and is inappropriate for work in the capillary realm, particularly so when the capillaries extend down to 30 to 50 micron internal diameter, and the flow rates are in the nanoliters-per-minute region.

A further disadvantage of that implementation is that the diaphragm booster stage imparted a significant AC pressure pulsation in the range of 100 PSIG, at the 10 Hz stroke frequency, to the downstream system. The existence of this AC pulsation in turn required the use of a compliant pulse damper in continuity with the diaphragm pump output stream, which is not desirable from several standpoints. Finally, because the system was designed to perform continuous solvent delivery at flow rates up to 5 milliliters per minute, as required for 4 mm ID columns, each of the intermediate-pressure solvent pumps was itself a continuous-delivery reciprocating pump comprising two cylinders and associated valving, resulting in a complex and expensive system.

Davis, M. T., et al., J. Am Soc. Mass Spectrom., 6, 571–577 (1995) describe an alternate implementation of a solvent delivery system designed to be operable at a capillary size scale. The approach disclosed by Davis et al. involves forming gradients by employing two low-pressure syringe pumps to generate a solvent composition which temporarily resides in a loop of open tubing. This loop is connected at each end to a commercially available six-port switching valve, following the manner of an external loop injector. Upon actuation of the switching valve, the fluid contents of the external loop are placed in continuity with the column, and with a high-pressure-capable syringe pump. The syringe pump is operated as a pressure source to expel the fluid contents of the external loop through the capillary analytical column. In arguing for a constant-pressure mode of operation, the authors acknowledge that their system is substantially incapable of constant-flow operation, as "There is no direct measurement of the actual flow from the column, and no feedback to the pump to maintain that flow rate. The piston is simply moved at a constant rate, and it can take a surprisingly long time for a system to come to equilibrium, and measured flow rates can change considerably during the course of a run." The system which Davis et al. describe includes a very large-volume syringe, representing a significant hydraulic capacitance, connected to a relatively small-diameter, and therefore substantially restrictive, capillary column. Such a system would indeed be expected to suffer from a very long hydraulic time-constant, or flow-rate settling time, in response to either a resistance change of the analytical column, or a flow-rate change at the syringe pump. This settling time could range from many minutes to hours. Therefore, for all practical purposes, during the course of a chromatographic run, there would be little correlation expected between the syringe pump delivery flow rate and the column flow rate. The authors claim that "there is no significant difference between constant pressure and constant flow operation when peptides and proteins are separated by capillary HPLC", yet acknowledge that during constant pressure operation, there are flow rate changes arising from the changes in solvent viscosity during gradient elution, and that constant-pressure operation is sensitive to "flow problems caused by sample precipitation or other blockage in the tubing or on the column".

In fact, when samples drawn from biological matrices are separated by capillary chromatography, it is not unusual to see the column resistance change measurably from one run to the next. This effect is superimposed upon the column resistance variation typically observed from one column to another, which is attributable to minor variations in physical construction and packing. Even small flow rate changes impair the user's ability to quantitate sample amounts from detector peak areas, since the area measurement assumes a constant flow rate. Larger flow rate changes impact system properties such as the ability to successfully maintain stable spray behavior in electrospray/nanospray interfaces. These examples illustrate why HPLC has been optimally practiced at constant volumetric flow rate as opposed to constant pressure. The Davis system provides the user with substantially no quantitative measure of the actual delivery flow rate provided to the column.

Finally, the approach disclosed by Davis et al. teaches the use of a loop of open tube as a gradient storage device. FIG. 3 in the Davis reference shows that there is only a very crude relationship between the called-for and the actual gradient composition profile delivered to the analytical column when a loop of open tube is used as the storage device. This behavior is not surprising in light of the fact that an open tube storage device will be susceptible to compositional band or zone broadening due to the Poiseuille flow profile attained in the open tube during fluid loading and expulsion, and to density-driven fluid motion while the solvent composition gradient is resident in the tube.

Recently, interest has developed in the ability to perform BPLC separations using extremely small diameter packing materials, that is, less than three micron diameter, with concomitantly high mobile phase pressure, which is required to drive the liquid through a bed filled with such packing particles. Enhanced separation characteristics of HPLC are demonstrated, in particular, either the absolute peak capacity of the separation, or the throughput of the separation as expressed in peaks eluted per unit time, can be substantially improved through the correct use of small packing particles and a high system pressure. The utility of particles as small as one micron diameter and system pressures in the rage of 10,000 to 100,000 PSIG has been demonstrated. However, in such analysis, power dissipation in the form of self-heating of the columns can be significant under the conditions of extremely high pressure drop over the length of the column. Therefore, it is desirable to maintain the column diameter as small as is feasible, often in the range of 30 to 75 micron internal diameter. These small column diameters, with correspondingly small volumetric flow rate requirements, help maintain the total heat generated to a relatively small value, and also keep the thermal paths for heat dissipation relatively short.

In using such small diameter columns (30 to 75 micron internal diameter), the actual volume of separation becomes exceedingly small, given that the mobile phase flow rates are typically in the 5 to 200 nanoliter per minute range. Gradient formation requires that the individual components of the mobile phase must be delivered at levels as low as 0.1% of the total system flow rate. In addition, high-pressure gradient formation pumps must deliver the component flows in a manner which is reproducible in fashion, against the full system operating pressure, without perturbations. The above described analytical requirements imply the ability to quantitatively deliver component flow rates as small as 10 picoliters per minute against pressures as high as 100,000 PSIG. Known HPLC systems do not provide the sealing and actuator technology required for the above stated requirements at a cost which is reasonable in the intended market.

Therefore, in light of the above, flow-splitting based systems have come under investigation for performing separations using extremely small packing particles with concomitantly high mobile phase pressure to drive the fluid through the bed of packing particles. These flow-splitting systems use solvent composition generation and pressure augmentation at a size scale of convenience. This larger scale flow is directed to a shunt path which includes significant resistance in line. The small scale gradient flow required for the above-stated 30 to 75 micron internal diameter columns is tapped from the larger scale flow by means of a tee and is subsequently conveyed through the injection means toward the column. Such systems have been employed extensively in capillary chromatography at modest pressures (0 to 5,000 PSIG) and their operation is being explored at more elevated pressures in the range of 6,000 to 20,000 PSIG. Drawbacks of these flow-splitting systems become apparent when system pressures reach the 50,000 to 100,000 PSIG levels, in part due to heat dissipation in the shunt path. In extreme cases, the heat generated is enough to convert the prescribed liquid into a vapor, or at a minimum, a liquid having a substantial vapor component.

Thus it should be apparent that the implementation of systems intended for use with extremely small packing particles and high mobile phase pressures involves severe design challenges.

SUMMARY

The present invention provides an HPLC solvent delivery system which accomplishes low volume solvent composition formation at a selected pressure, for example, at substantially atmospheric pressure. Such low volume, low pressure solvent composition formation is followed by pressurization of the formed solvent composition, which is in turn followed by expulsion of the formed solvent composition at a higher pressure into a receiving device such as a column. The formation of the solvent composition at low pressure can also include the introduction of the sample analyte as a step or process included within the solvent composition formation.

According to the invention, a high pressure capillary liquid chromatography solvent delivery apparatus and method uses low volume solvent composition formation at a selected pressure, for example, at substantially atmospheric pressure, followed by pressurization of the formed solvent composition. The solvent composition formation is performed at a substantially low volume and a selected pressure, for example, at substantially atmospheric pressure, and is then pressurized. Expulsion of the formed solvent composition is then effected at this higher pressure into a receiving device such as a column. The solvent composition is formed from a solvent composition generator or fluid metering system which may be optimized to deliver liquids at low pressures into a receiving solvent composition storage matrix via an isolation valve. The solvent composition delivered to the storage matrix is in reverse order such that the first volume of the solvent composition delivered to the storage matrix is the last volume of the solvent composition expelled out. The solvent composition so formed can include sample analyte introduced via a low-pressure injector, the sample volume existing as a band or zone within the formed solvent composition. Pre-existing liquid within the storage matrix is displaced into a compliant, variable-volume fluid accumulator such as a pleated bellows or a diaphragm, which is in fluid communication with the storage matrix. The fluid accumulator is enveloped in a pressure caisson or chamber which can be pressurized or depressurized in response to sensor signals obtained from a fluid volume displacement transducer (or sensor) responsive to the volume change of the fluid accumulator, and in response to a pressure sensor in fluid communication with the caisson, in accordance with solvent composition cycle formation. Closure of the isolation valve isolates the solvent composition generator, and the low-pressure injector, if present, from the pressures developed during the solvent composition pressurization and expulsion phases of system operation. As the caisson is pressurized, the solvent composition within the storage matrix is expelled out past the isolation valve by the pressure acting on the fluid accumulator and its fluid contents. The solvent composition is then delivered to the chromatographic column via a path which can include a high-pressure capable injector.

Advantages of the present invention include operability at pressures above normal HPLC operating pressures, with the potential to utilize smaller chromatographic packing particles, in order to obtain enhanced separation characteristics of the chromatographic system, including improvements in the absolute capacity of the separation and/or the throughput of the separation as expressed in peaks eluted per unit time. The system and method are scaleable, and can be used with relatively more moderate pressures and column internal diameters. When employed with suitably small columns and volumetric flow rates, the total power dissipation resulting in heat generation within the column can be kept relatively small, and the associated thermal paths for heat dissipation can be relatively short.

Another advantage of the high pressure capillary liquid chromatography solvent delivery system is that it is operational at elevated pressures without the use of dynamic seals exposed to high pressure whose failure would give rise to compositional fluctuations or errors. Rather, the system may be constructed using a single dynamic seal at the pressure caisson, whose sealing performance is non-critical, in that, the actuator rate being applied to the piston which pressurizes the caisson is not used to infer the delivery flow rate.

In the gradient mode of chromatography, peak retention behavior is primarily dictated by solvent composition and according to the invention, the accuracy of maintaining the solvent composition profile is enhanced by the fact that this profile is generated under conditions of substantially constant and relatively low pressure, where the fluid metering behavior can be optimized. If syringe pumps are employed to perform this low-pressure fluid metering function, their behavior can be optimized because the low axial loads on the syringe pump pistons permit the use of drive screws with micrometer-quality threads, at relatively modest cost, and obviate the need for heavy thrust bearings which can degrade the accuracy of the syringe piston linear translation mechanism. The syringe pump seals are not subjected to high loads which would result in either excessive seal leakage or significant seal deformation. The fact that the fluid metering leading to solvent composition formation is accomplished at low pressure, enables the use of alternate fluid metering technologies, including those which are normally constrained to work at pressures near atmospheric pressure, an example being integrated microfluidic dispensing or delivery systems which utilize one or more diaphragm-style pumping elements typically actuated by solenoids or piezo-electric actuators.

Because the short-term flow rate through the chromatographic column is governed by caisson pressure, which is monitored and controlled via feedback loop, the requirements for translational accuracy imposed on the lead screw or jack mechanism actuating the caisson piston are relatively simple. This is in contrast to lead screw requirements which exist for high-pressure solvent composition generation mechanisms used in current capillary liquid chromatography systems.

A further advantage of the presently disclosed chromatography system and methodology includes features drawn to stopped-flow spectroscopic scanning. The system allows for the solvent liquid flow, and therefore chromatographic peak elution, to be intermittently stopped, whereupon the caisson is rapidly depressurized and repressurized under pressure servo control without substantially varying the compositional attributes of the emerging solvent composition.

An additional advantage of the present invention derives from employing a series pump architecture in a manner that minimizes delay volume associated with the pressure boosting stage of the solvent delivery process. The formed solvent composition flows off the storage matrix directly into the analytical column, being displaced from the storage matrix by the reintroduction of fluid previously resident within the accumulator. Moreover, the solvent compositions in the present invention can be formed at a flow rate convenient to the protocol being employed. Typically, the solvent composition formation flow rate is multiple (many) microliters per minute, while the expulsion flow rate may be only a few nanoliters per minute. These two processes are decoupled in time, allowing the fluid metering elements to perform in a flow regime where their behavior is more nearly ideal.

Another feature attendant to the present invention is that only a single dynamic seal is maintained in the pressurized portion of the system. Additionally, its leakage characteristics, short of outright seal failure, are substantially decoupled from the chromatographic delivery, in that both the caisson pressure, and the volumetric delivery during fluid transfers into and out of the storage matrix, are independently measured. Further, the fluid accumulator allows fluid displacement to occur into or out of the storage matrix while implementing a hermetic-quality barrier between the working fluid within the caisson and the chromatographic stream.

Still another advantage to the present invention is the ability to generate and store the solvent compositions for an entire chromatographic run, due to the diminutive scale of capillary chromatography, and therefore, it is not of necessity to have continuous-flow metering pumps to form the solvent compositions at run-time as is true in other commercial systems. This contributes to the overall simplicity of the current chromatography system.

The herein described high pressure capillary liquid chromatography solvent delivery system and methodology is capable of providing reasonable solvent delivery operation at both low and high pressure extremes which are unattainable with present HPLC systems. The present invention is particularly well-suited for systems directed to high peak capacity separations employed in coupled liquid chromatography-mass spectrometry (LC-MS) and the like.

BRIEF DESCRIPTION OF THE DRAWINGS

The foregoing and other features and advantages of the present invention will be more fully understood from the following detailed description of an illustrative embodiment, taken in conjunction with the accompanying drawings in which.

DETAILED DESCRIPTION

An illustrative embodiment of the apparatus and method disclosed herein is discussed in terms of liquid chromatography, specifically, solvent composition formation and delivery for high pressure capillary liquid chromatography. It is envisioned, however, that the disclosure is applicable to a wide variety of procedures and apparatuses, including, but, not limited to, elution liquid control, fluid metering, mixing and composition control systems, multiple solvent delivery, spectroscopic studies, solvent composition generators and the like.

In the discussion which follows, the term "syringe" or "syringe unit" will be herein defined as one or more cylinders, each with its associated piston, piston seal, piston actuator, and, optionally, pressure sensor. A syringe, with its associated valve means including valve and valve actuator, will constitute a "pumping unit" such as described in commonly owned U.S. Pat. Nos. 5,897,781 and 5,637,208, which are incorporated by reference herein in their entirety. The present invention may employ the use of one or more pumping units, to serve the low pressure fluid metering function. In the context of the present application, the term "metering unit" will be used interchangeably with the term "pumping unit". It should be appreciated that the term "metering unit" may be construed to refer generally to fluid dispensing or delivery systems of various configurations as used herein.

Figure 1:
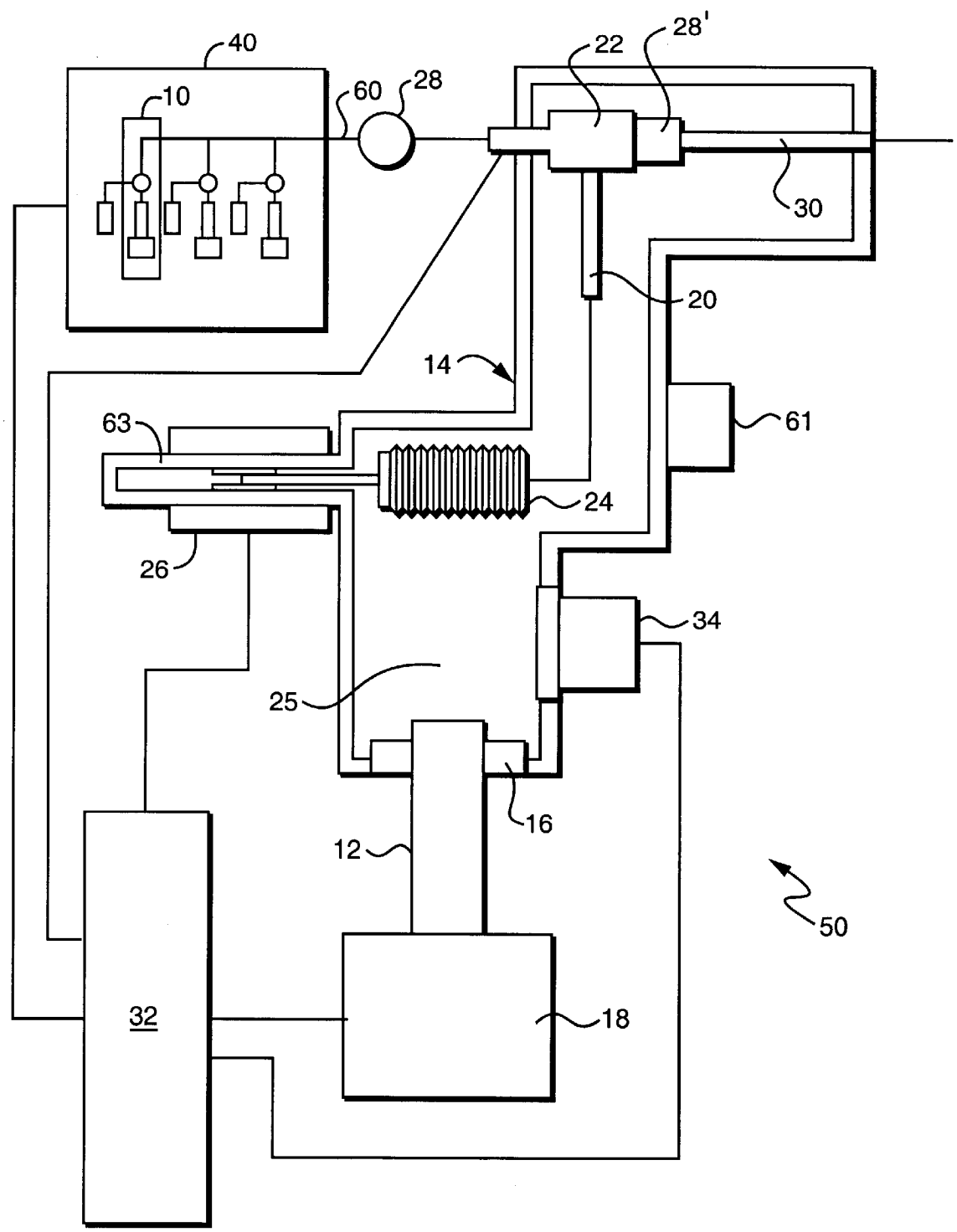
FIG. 1 is a block diagram of a high pressure capillary liquid chromatography solvent delivery system comprising a solvent composition formation sub-system, low-pressure sample injector, isolation valve, caisson, storage matrix, fluid accumulator, fluid volume displacement transducer, pressure sensor, piston and piston actuator, and optional high-pressure sample injector according to the present invention.

As illustrated in FIG. 1, a high pressure capillary liquid chromatography solvent delivery system 50 includes an isolation valve 22 coupled between a solvent composition generator 40 and a pressurized caisson chamber 14 acted upon by a piston 12. The linear motion of the piston 12 sweeps out a volume within the caisson 14. Hydraulic sealing between the piston 12 and the caisson 14 is brought about by a dynamic seal 16, which resides in a cavity within the caisson 14 and which interfaces with the outer diameter of the piston 12. The force to drive the piston 12 is derived from a motorized mechanism, including stepper motor 18, and associated rotary-to-linear drive conversion elements as described in U.S. Pat. No. 5,637,208. The stepper motor 18 is optimally driven in microstep mode and may include a reduction gear module to further reduce the magnitude of the smallest incremental piston motion attainable. Stepper motor 18 provides rotary motion which is converted to linear motion by a lead screw spindle and nut arrangement (not shown). The stepper motor 18 rotates the nut which is supported by bearings (not shown) which provide both radial and axial support to the nut to thereby decouple the hydraulic forces which are asserted axially onto the lead screw and nut from the stepper motor 18. The lead screw is free to move axially through a defined range, but is prevented from rotating by an anti-rotation element, such technique being commonly known to those skilled in the art. The lead screw couples to the piston by means of a bearing which transfers the axial force while maintaining relatively precise axial alignment along the driven end of the piston 12.

With continuing reference to FIG. 1, the caisson 14 provides a fluid tight containment around an axially extensible, accordion-like bellows 24 constructed of highly compliant material such as thin, convoluted metal or the like. The bellows 24 is constructed without dynamic or sliding seals, such that its resistance to deformation during fluid transfers does not require the pumping or metering units 10 to pump against significant pressures. The high-pressure capillary liquid chromatography solvent delivery system 50 provides operation at elevated pressures without the use of multiple dynamic seals exposed to high pressure, whose failure would give rise to compositional fluctuations or errors. Rather, the system 50 may be constructed using the single dynamic seal 16 exposed to high pressure, whose sealing performance is non-critical, in that, the actuating rate applied to the piston 12 as it pressurizes the caisson 14 is not used to infer the chromatographic delivery flow rate.

The pressure caisson 14 can be pressurized or depressurized in response to solvent composition cycle formation and sensor signals obtained from a pressure transducer 34 and a fluid volume displacement transducer (or sensor) responsive to volume changes of the fluid accumulator, such as a linear variable differential transformer (LVDT) 26. The fluid accumulator 24 has one fixed end, nearest to the storage matrix, and one end which moves in response to fluid volume transferred into or out of the accumulator. The core of LVDT 26 is coupled to the moveable end of fluid accumulator 24 and a signal derived from LVDT 26 is directed to a processor 32 which also controls the volumetric delivery of the metering units 10. (Note: signal lines drawn to the processor or controller 32 are merely illustrative and not intended to show comprehensive signal paths.) The distending motion of the accumulator 24 enables a signal derived from LVDT 26 to be used for calibrating the relationship between accumulator displacement and volumetric delivery of the metering units 10. This signal can be combined with solvent composition cycle formation information for precisely controlling the metering units 10 and piston 12. It is important to note that the accumulator 24 serves as an isolation envelope between the formed solvent composition, that is, the fluid contents of the storage matrix 20 and the fluid contents of the pressure caisson 14. Thus the composition of the immersing fluid 25 can be different from the formed solvent composition 60. A fill port 61 is included in the present invention. The fill port enables the caisson to be initially filled with liquid. Additionally, the fill port allows for the replenishment of liquid over time should there be any loss of liquid due to leakage from the caisson. Optionally, a check valve can be positioned at the fill port 61, which connects the fill port 61 with a reservoir of the immersing fluid 25. This arrangement would allow for the replenishment of immersing fluid to be performed automatically during caisson decompression cycles.

The linear variable differential transformer or LVDT is a 'non-contacting' form of displacement measurement. The term 'non-contacting' is used herein to convey the concept that the core of the LVDT (typically a nickel-iron cylinder, which is attached to the moveable end of the fluid accumulator by a short actuator rod) does not need to be in mechanical contact with the housing of the LVDT, where the excitation and sense coils are located. Specifically, there is an electromagnetic coupling between the excitation coil and the core, and between the sense coils and the core. In the present invention, a thick-walled, non-magnetic stainless steel tube 63 is interposed between the LVDT core and the LVDT housing, such that only the core of the transducer resides within the high-pressure caisson; all the remaining transducer components are located outside the caisson. In order that no dynamic sealing is required to support the displacement measurement, the intervening thick-walled stainless steel tube 63 is made part of the caisson structure.

The isolation which exists between the chromatographic stream, which may comprise aggressive solvents, and the immersing fluid of the caisson, allows for the selection of an immersing fluid within the caisson which is independent of the composition of the chromatographic stream. With appropriate selection of the immersing fluid, for example, a non-corrosive, non-electrically-conductive liquid, one may choose to place the displacement transducer inside the caisson and then route the electrical contacts out through statically-sealed bulkhead fittings as is known in the art. In the case of an LVDT, the housing can be penetrated by ventilation holes, and the LVDT can be run with "wet coils", as is known in the art. Alternatively, other forms of displacement measurement are enabled by appropriate selection of an immersing fluid, including capacitance-type transducers, linear optical encoders, resistive/potentiometric transducers, and the like. In none of these cases would it be required to carry a high-pressure dynamic seal through the caisson wall in order to effect the displacement measurement. Finally, while an LVDT is well suited to measurement of the elongation and contraction of a cylindrical bellows which is responding to fluid transfers into or out of the storage matrix, it will be recognized that other fluid accumulator geometries and materials, such as an elastomeric diaphragm, may be better coupled with alternate means of inferring fluid volume displacement, such as a strain gauge.

The pressure caisson 14 is capable of being pressurized and depressurized by a pressure source such as a motorized mechanism (described above) which displaces the piston 12 through the seal 16 to thereby compress immersing fluid 25 within the caisson 14. The pressure inside the caisson 14 is monitored by a pressure sensor 34 of appropriate scale as is known in the art. It is important to note that, if a dynamic or sliding seal 16 is utilized at the point of entry of the piston 12 into the pressure caisson 14, the effect of seal leakage can be mitigated by controlling the actuation of the piston 12 in a pressure servo mode such that the caisson pressure is maintained at a set point value which is substantially independent of a small and potentially variable seal leakage rate.

Figure 2:
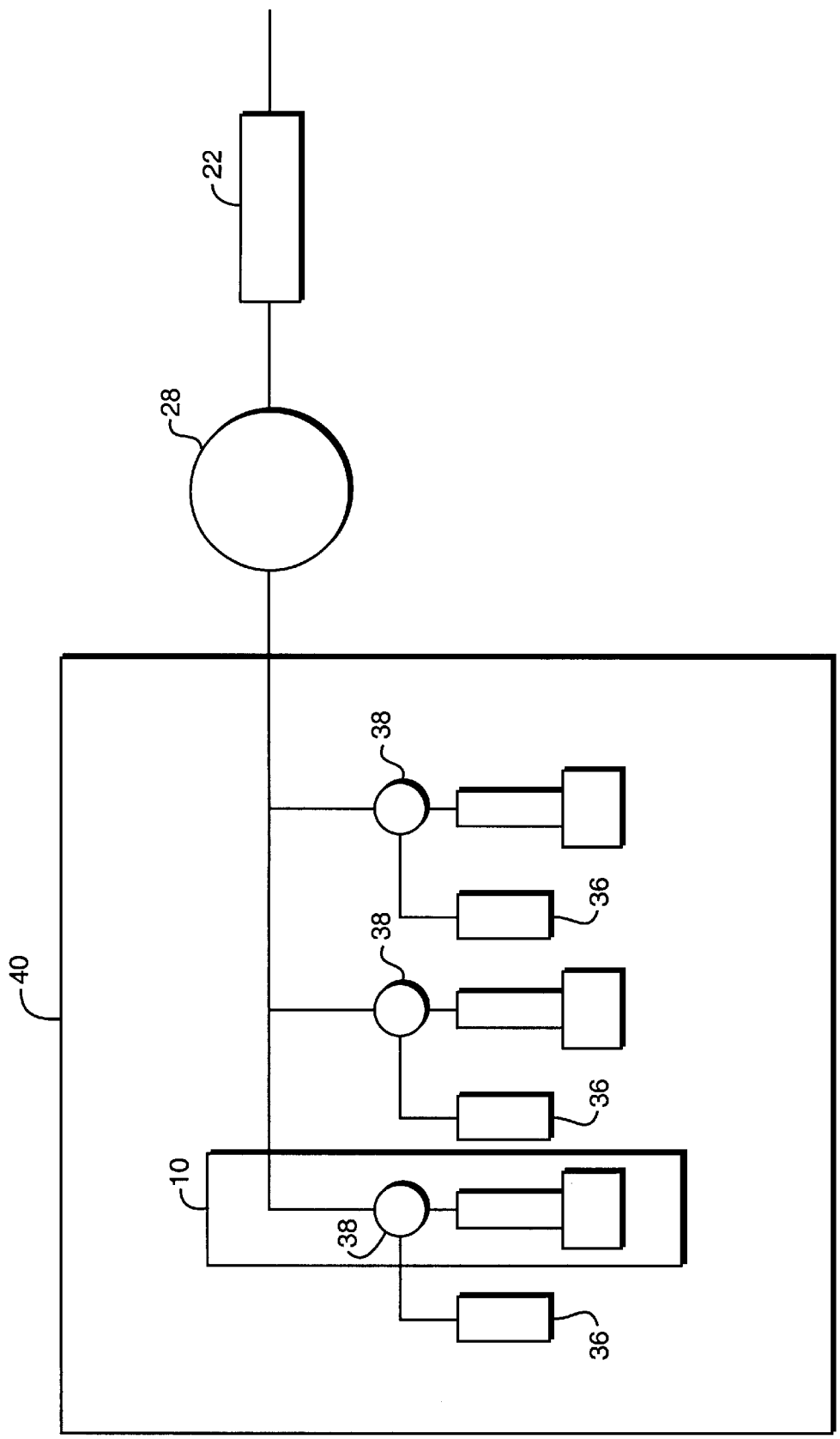
FIG. 2 is a block diagram of a ternary-capable solvent composition formation sub-system comprising three fluid metering units.

With reference to FIG. 2, a solvent composition generator 40 is disclosed as having a plurality of metering units 10, as previously described above and as is known in the art. The metering units 10 are configured to deliver liquids at low pressures for the formation of solvent compositions 60 at low volumes and pressures as associated with the present disclosure, in that, utilization of known syringe control techniques currently applied to capillary chromatography would also apply to metering units as disclosed herein. The metering units 10 are driven against substantially atmospheric pressure, or against slightly elevated pressure in the neighborhood of one to several atmospheres, that pressure being held substantially constant throughout the solvent composition formation process by means of the pressure servo control acting upon piston 12.

Each metering unit 10 includes low pressure valving 38 which is designed to enable the intake of solvent from respective solvent reservoirs 36 and subsequently the expulsion of solvent through injection valve 28 and then to a high pressure capable isolation valve 22. The isolation valve 22 includes a relatively low internal volume and high pressure-sealing characteristic, and can be constructed, for example, on the principle of a rotary or linear face-seal valve, a rotary spool valve, or a needle valve. The valve can be actuated by a pneumatic amplifier/actuator or by electromechanical means, as is known in the art. In the case of systems directed to extremely small volume gradient formation, the isolation valve function can be implemented by the technique of freeze-thaw flow management, an example of which is described by Bevan, C. D. and Mutton, I. M. Anal. Chem. 67, 1470–1473 (1995). Use of this approach obviates the need to interpose any additional mechanical valve hardware into the wetted solvent path, conferring advantages with respect to minimizing valve-induced broadening of small-scale compositional features or injected sample bands.

Referring back to FIG. 1, the solvent composition 60 is expelled from the metering units 10 at low pressure to a receiving storage matrix 20 via the high-pressure capable isolation valve 22. In an illustrative embodiment, the storage matrix 20 comprises a bed packed with approximately 5 micron diameter beads of fused silica. The storage matrix 20 may be packed with substantially chemically inert particles such as quartz or ceramic solid spheres, or may be packed with particulates which may include an extended, chromatographically-active surface, as would be obtained with porous silica particles coated with a bonded phase, as in a chromatographic packing material. Alternatively, the bed may be packed with porous or permeable membrane elements, or other matrix which serves to stabilize and preserve the formed solvent composition profile during periods of fluid transfer and fluid residence within the matrix. In the case of systems directed to extremely small volume gradient formation, the storage matrix 20 may comprise a microfabricated structure incorporating an array, or plurality of arrays, of fluid passageways integrated on a solid support or substrate.

The solvent composition 60 is delivered to storage matrix 20 in reverse order, such that the first volume of solvent composition 60 delivered to storage matrix 20 is the last volume of solvent composition 60 expelled from storage matrix 20. Pre-existing liquid within storage matrix 20 is displaced into accumulator 24 in fluid communication with storage matrix 20. In a high-pressure to ultra-high-pressure system, it is an advantage to remove or isolate as many sealing surfaces as possible from exposure to the high pressure. This is particularly true in the case of an injection valve, as injection valves are typically located in-line in the analytical stream, and are required to possess properties of extremely low band-broadening contribution, a high degree of chemical inertness, and a low seal shedding rate (to avoid plugging of the analytical capillary column with particulates). The requirements imposed upon hydraulic valves elsewhere in the system, for example, valves associated only with working fluid 25, are less severe, and alternative valve geometries are available for these purposes. The present invention allows for the option of locating the injection valve 28 immediately downstream of the metering units 10 on the low-pressure side of the system, thereby allowing for low pressure injector operation. There are a variety of valve materials and valve geometries available which are suitable for use at low pressures. Additionally, there can be operational advantages which result from not exposing the injection loop (where sample take-up occurs) to high pressure. When a conventional injector is actuated, the sample loop is alternately exposed to system pressure and to atmospheric pressure, resulting in significant compression and expansion of the loop contents, which in turn can impair the ability of the injector to perform small-volume sample take-up quantitatively.

In the present invention, the placement of the injector hardware permits sample uptake and sample introduction into the chromatographic solvent environment to occur in a regime of substantially atmospheric pressure. The sample and its solvent environment are subsequently transported to the storage matrix 20 where the pressurization step occurs.

The pressurization occurs only after the entirety of the sample has been introduced to the fluid stream, and only after the injection hardware has been isolated from the high-pressure environment by actuation of the isolation valve 22. The injection valve 28 is thus free to be returned to its loop loading state with substantially no decompression of the loop contents required, that is, in readiness to perform another quantitative take-up of sample. A further advantage in gradient chromatography is that in many cases, the injected sample can be concentrated at the head or inlet end of the analytical column under the initial or weakly-solvating conditions of the gradient, resulting in a focussing or narrowing of the injected band from the standpoint of the volume over which it is dispersed. This focussing mechanism can be used to minimize any band broadening which may have occurred in the transit of the sample through the high-pressure isolation valve 22.

There can be operational modes, particularly in isocratic chromatography, where the narrowest possible injected band of sample is desired to be placed on the column, and an on-column focussing mechanism may not be available. In this case, a high-pressure-capable injection valve 28' can be placed in-line in the alternate location shown (in FIG. 1), that is, between the storage matrix and the analytical column. This placement immediately upstream of the chromatographic column mimics the hydraulic arrangement of conventional chromatography systems with regard to injector placement.

Under the conditions described above, extremely small volumes of mobile phase comprising solvent composition 60 can be displaced out of one or more metering units 10, with extremely fine resolution. A plurality of these metering units 10 can be used to form the solvent composition 60 in a hydraulic configuration which resembles conventional high-pressure gradient formation. However, the metering units 10 are delivering fluid via isolation valve 22 into a substantially fixed receiving pressure of relatively small magnitude within storage matrix 20. This hydraulic configuration is different from conventional scale "low pressure gradient formation" which is not operable at the size scales referenced above. An advantage of causing the metering units 10 to deliver into a very low receiving pressure is that the associated valves, valve actuators, piston drive elements, seals and the like can be designed specifically for low pressure operation and can be simpler, less costly, or potentially longer lived than known devices which are designed to be operable at pressures in the thousands of PSIG. An example of an alternate form of fluid metering enabled by the existence of a low receiving pressure at storage matrix 20 would be the use of microfabricated fluid dispensing technology, comprising one or more channels of diaphragm-type fluid pumps implemented on a common substrate, and actuated by solenoid or piezo-electric actuators, as is known in the art.

The delivery of one or more metering units 10, operating at controlled rates over time, will result in the creation of a volume of liquid having a controlled composition characteristic as a function of time and therefore as a function of volume delivered. A benefit of the small scale of capillary chromatography is that the absolute or total volume of a given chromatographic separation is correspondingly small and therefore manageable as compared to other known forms of liquid chromatography. Upon delivery of the metering units 10 and subsequent formation of solvent composition 60 into storage matrix 20, the spatial characteristics of the formed solvent composition 60 will be substantially preserved. Specifically, the pattern of composition change over time which causes spatial variation in composition can be preserved in the storage matrix 20 for a usable period of time, i.e., minutes to hours.

The preservation of the fidelity of compositional zones or bands is fundamental to the practice of chromatography. In using an appropriate choice for the overall dimensions for storage matrix 20, and an appropriate choice for the fluidic permeability of the matrix, the source pressure requirements to meet the desired storage matrix filling rate can be held to a suitably low value. In this particular embodiment, the solvent composition 60 is formed "in reverse" into the storage matrix 20, because the sequence of operations will cause the liquid flow into and out of the storage matrix 20 to be "last in" and "first out". The formation of solvent composition 60, in reverse, into storage matrix 20 will cause the displacement of the liquid currently residing in the storage matrix 20 into the fluid accumulator 24. Due to the highly compliant nature of the fluid accumulator 24, the metering units 10 are not required to pump against significant additional pressure; therefore, allowing the fluid accumulator 24 to distend into the enclosing volume of the pressure caisson 14. The fluid volume within the pressure caisson displaced by the distension of the accumulator will be accommodated by retraction of the piston 12, which can be operated in a pressure servo mode so as to maintain caisson pressure substantially constant throughout the storage matrix loading process. Alternatively, the caisson could simply be vented to atmosphere during the storage matrix loading process, for example, through the use of a vent valve in fluid communication with fill port 61.

The combination of actions undertaken by the metering units 10 and piston 12 results in the formation of solvent composition 60. Upon completion of formation of the solvent composition 60, each of the metering units 10 switches its respective low pressure valve 38 to undertake a fill cycle to replenish its liquid contents from its respective solvent reservoir 36. At this time, the high-pressure capable isolation valve 22 is switched, such that the metering units 10 and injection valve 28 are isolated off-line from the storage matrix 20. Upon the isolation of the metering units 10, and the injection valve 28, pressure caisson 14 is pressurized in order to begin driving the formed solvent composition 60 out from storage matrix 20. As described earlier, the pressure of the caisson 14 is derived from the displacement of fluid 25 by the motion of piston 12 through seal 16.

As the caisson 14 is pressurized, solvent composition 60 within the storage matrix 20 is compressed by the pressure acting on the fluid accumulator 24 and its fluid contents. When thus pressurized, the solvent composition 60 begins to be delivered past the isolation valve 22 toward a receiving system which will typically comprise the chromatographic column 30, and may include a high-pressure capable injector 28. As the solvent composition 60 is first compressed and subsequently expelled, the fluid accumulator 24 inside pressure caisson 14 will begin returning to its non-distended shape. The LVDT 26 will respond by indicating the displacement of the moveable end of the accumulator. The controller 32 can then monitor the LVDT output as a function of time.

Figure 3:
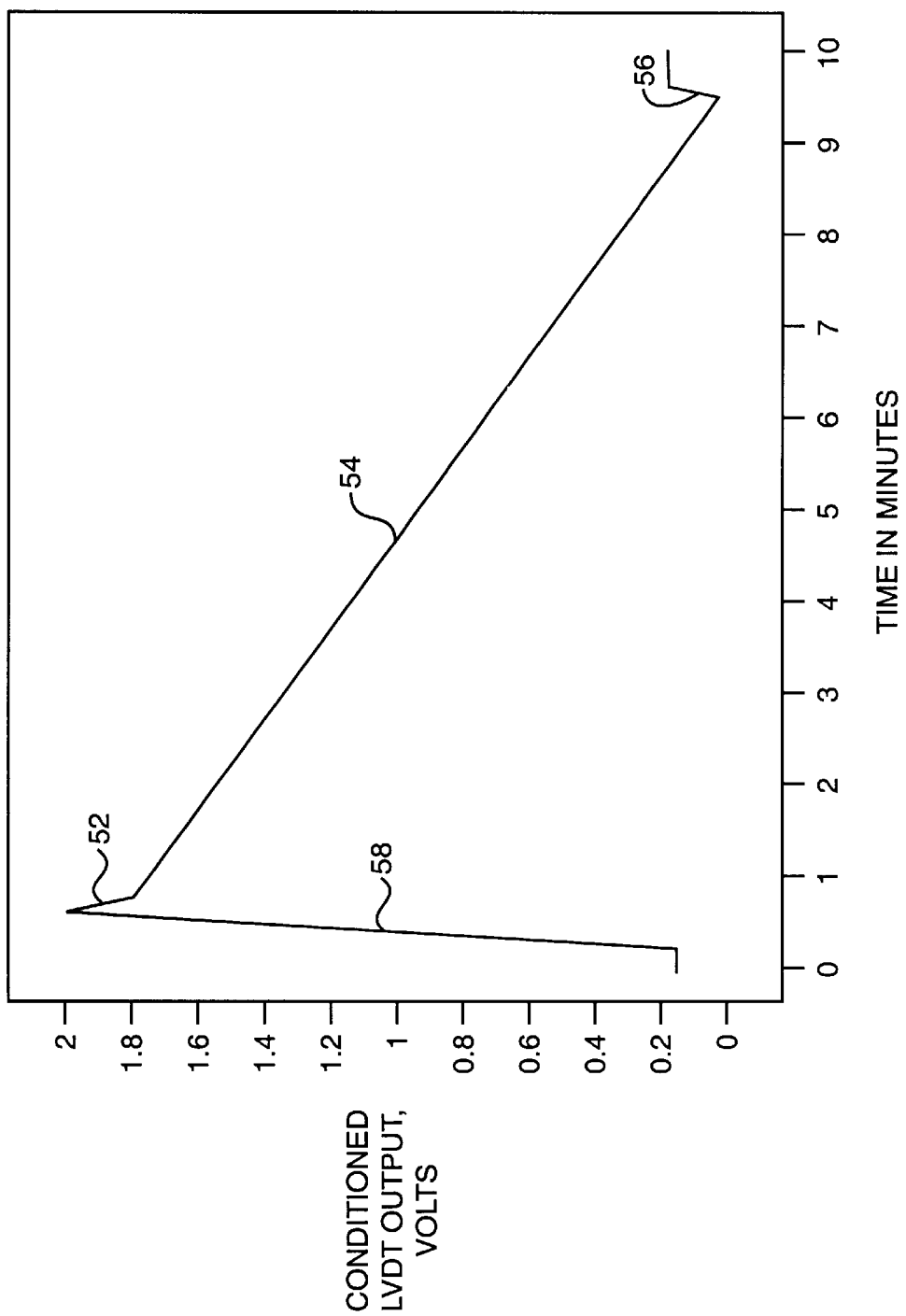
FIG. 3 depicts a conditioned voltage output of a linear variable differential transformer (LVDT), implemented as the fluid volume displacement transducer in the embodiment of FIG. 1.

FIG. 3 depicts the conditioned voltage output of the LVDT, over an interval of time which includes a solvent composition formation sub-interval 58, a solvent compression sub-interval 52, a solvent expulsion sub-interval 54, and a solvent decompression sub-interval 56. It will be noted that when the caisson is initially pressurized, in preparation for the expulsion of the formed solvent composition 60, there is a sub-interval 52 where the LVDT output reflects that accumulator motion which is associated with the initial compression of the fluid contents of the fluid accumulator 24 and the storage matrix 20. The pressurization of the caisson which accomplishes this initial fluid compression step is typically undertaken using a rate of volumetric displacement at piston 12 which is very much higher than the volumetric flow rate to be delivered out through the resistance of the chromatographic column. As a result, as the initial pressure setpoint in the caisson is reached, and pressure is stabilized under servo control, there is a substantially sharp inflection detected in the rate of change of the LVDT output with respect to time. That is, the initial solvent compression step may be undertaken at an almost arbitrarily fast rate, using a rate of displacement at piston 12 corresponding to a volumetric flow rate of hundreds of microliters per minute. Once the caisson pressure setpoint is achieved and the pressure value is stabilized, there is, substantially instantaneously, no further fluid accumulator displacement associated with this initial fluid compression event, and subsequent fluid accumulator displacement is then associated with solvent flow directed out through the chromatographic column.

In the case of an accumulator which is constructed from a pleated metal bellows, and which is operated over a stroke length which is short relative to the length of the bellows, there is a substantially linear relationship between bellows length and bellows internal volume. Therefore, under the condition of constant pressure, there is a corresponding, substantially linear relationship between LVDT output and fluid volume delivered into or out of the accumulator. Under this condition, the rate of change of LVDT output with respect to time is reflective of the volumetric flow rate into or out of the bellows, via a calibration curve which can be constructed during the storage matrix loading phase of operation, when the metering units are metering solvent into the storage matrix 20. This operation is performed at a substantially constant pressure, and creates a distension of the bellows, which is monitored by the controller 32, from the output of the LVDT.

During the solvent expulsion phase of operation, the rate of change of LVDT output with respect to time can be used to compute the delivery flow rate of mobile phase through the analytical capillary column. This delivery flow rate can be incorporated into a feedback control strategy, as detailed below, thereby permitting the system overall to function as a volumetric solvent delivery system, as opposed to a constant-pressure solvent delivery system.

The flow rate computation must be performed in a manner which discriminates accumulator motion associated with solvent compression from accumulator motion associated with mobile phase delivery through the analytical column. It is recognized that whenever caisson pressure is changed, the column of fluid residing within the accumulator and the storage matrix must undergo a corresponding compression or relaxation, thereby affecting the displacement detected by the LVDT. This column of fluid acts like a spring interposed between the moveable end of the accumulator and the solvent front which is being forced through the analytical column. During any interval of time where the caisson pressure is held to a substantially non-varying value, the column of fluid does not compress or relax, that is, it behaves as if it were an infinitely stiff spring. At least two techniques are available to the controller 32 to discern the analytical column flow rate during the changing pressure regime common to gradient chromatography. In a first technique, the controller time slices its observation of the LVDT output, such that a flow measurement interval is alternated with a pressure controller setpoint change interval. This approach takes advantage of the fact that in a microprocessor-based control implementation, updating of the pressure control loop setpoint or reference level will occur at discrete time intervals, established by the microprocessor's programming. The pressure control loop itself can be implemented with a fast settling time, such that the response to a pressure setpoint or reference level change is extremely rapid relative to a chromatographic time frame. This allows the controller to implement a setpoint change, delay for the duration of a specified window for pressure loop settling, and then record a flow rate during a subsequent window where the accumulator displacement measurement occurs under conditions of constant pressure. In this arrangement, the controller has access to a discretely updated stream of flow rate measurements, available in substantially real-time, which will feed the flow control loop as detailed below.

In a second technique, the controller utilizes the direct measurement of hydraulic capacitance which it observes when it pressurizes (52, FIG. 3) the caisson prior to the start of a chromatographic run 54, and/or when it depressurizes 56 the caisson at the end of a chromatographic run. Specifically, the controller has the ability, through use of the caisson pressure sensor output and the accumulator displacement sensor output, to characterize the hydraulic capacitance presented by the combined fluid contents of the accumulator, the storage matrix, and the chromatographic column. In practice, the hydraulic capacitance presented by the fluid contents of the accumulator and storage matrix will typically dominate the total capacitance measurement and, in particular embodiments, the fluid contents of the accumulator alone will represent the dominant hydraulic capacitance. The controller can record the relationship between caisson pressure and accumulator displacement at the beginning of a run, when the accumulator has the largest enclosed fluid volume, and at the end of a run, where the accumulator has the smallest enclosed fluid volume. The controller may then encode a lookup table defining the hydraulic capacitance presented at each of these two extremes of operation, and can extract by interpolation the capacitance which would be presented at any intermediate point in the run. In a particular implementation, there is a substantially linear relationship which can be defined between caisson pressure and accumulator displacement, characterized by a slope value. To the extent that there may be small deviations from linearity in a particular system, the slope value can be computed specifically in the vicinity of an intended pressure operating point, thereby rendering the deviation from linearity substantially insignificant. A slope value thus calculated, which is associated with a specific accumulator displacement position such as the beginning or the end of chromatographic delivery, can be stored in memory. Interpolation may then be used to extract a valid slope value indicative of the hydraulic capacitance presented at any intermediate point in the chromatographic run. With this characterization of the hydraulic capacitance available, the controller can compute valid flow rate measurements even during intervals where the caisson pressure is changing. Specifically, by recording the pressure change which has occurred during the interval over which an accumulator displacement measurement was made, the controller can subtract from the measured accumulator displacement the contribution attributable to the compression or relaxation of the fluid contents in response to the pressure change. The resulting value reflects that accumulator displacement attributable to actual mobile phase flow leaving the storage matrix. Use of this second technique allows for valid flow measurements to be made even during the intervals in which caisson pressure setpoints are being adjusted. As with the first technique described above, the controller has access to a discretely updated stream of flow rate measurements available in substantially real time which will feed the flow control loop as detailed below.

It should be noted that in a microprocessor-based system, it is not a requirement that the relationship between displacement or distension of the fluid accumulator and the volume of fluid transferred into or out of the accumulator correspond to a linear calibration curve. A non-linear calibration curve can be readily accommodated by means of a look-up table or by curve fitting techniques as are known in the art.

It is at the option of the controller 32 to operate the system 50 during chromatographic delivery either in a constant pressure mode, that is, maintaining a constant setpoint pressure in the caisson 14, or by operating in a volumetric delivery mode, where the controller 32 additionally makes use of the flow rate information obtained as described above. In the volumetric delivery mode, the system 50 functions in an analogous manner to what is described in U.S. Pat. No. 4,767,279 to Dourdeville and Trumper, incorporated herein by reference in its entirety, wherein there is an inner pressure feedback loop for short term flow rate stability, encompassed by an outer, inferred flow feedback loop responsible for setting the reference level for the inner feedback loop so as to drive the inferred flow rate in accordance with the flow set point established by the operator.

In another illustrative embodiment, the presently disclosed chromatography system 50 includes operational features drawn to stopped-flow spectroscopic scanning. In this mode of operation, the solvent composition 60 flow can be stopped, wherein the caisson 14 is rapidly depressurized and repressurized under pressure servo control, without substantially varying the compositional attributes of the emerging solvent composition 60. Accuracy of maintaining a composition profile is enhanced by the fact that the composition profile is generated under conditions of substantially constant and relatively low pressure where the metering behavior of the metering units 10 can be optimized. Similarly, because the short-term flow rate through the chromatographic column 30 is governed by caisson pressure, which is under closed-loop servo control, responsive to the pressure sensor 34, the translational accuracy requirements imposed on the mechanism actuating the caisson piston 12 are relatively minimal.

Figure 4:
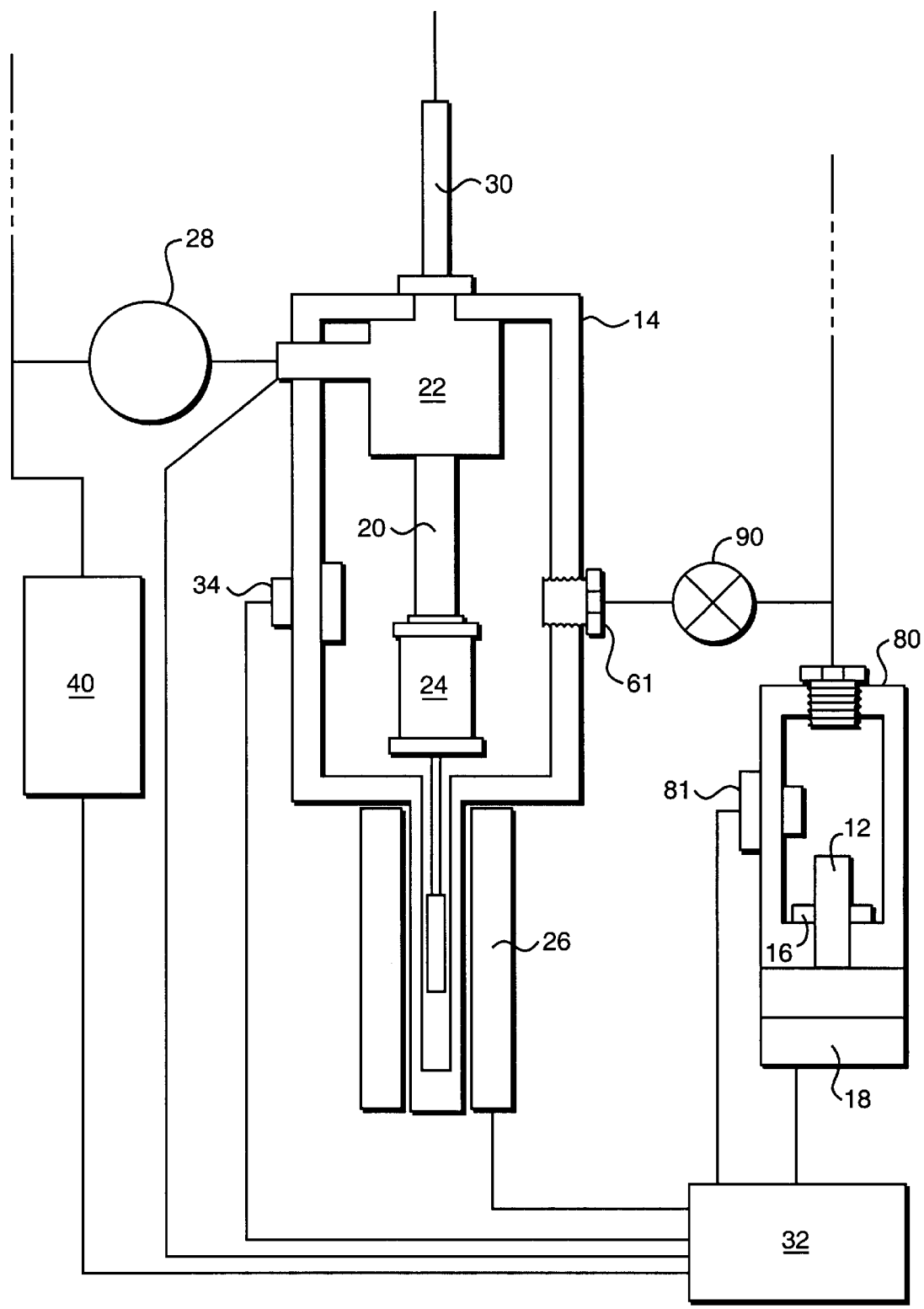
FIG. 4 is a block diagram of an alternative embodiment of the invention.

In another illustrative embodiment illustrated in FIG. 4, a caisson 14 can be constructed which includes only an isolation valve 22, a storage matrix 20, a fluid accumulator 24, a fluid volume displacement sensor 26, a fluid port 61, and optionally, a pressure sensor 34. The caisson 14 can be connected via its fluid port 61 to a remote pressurization source 80. In this illustrative embodiment, remote pressurization source 80 includes a piston 12, a seal 16, a step motor 18 driving piston 12 through rotary-to-linear drive conversion elements (not shown), and a pressure sensor 81. Pressurization source 80 is commanded to provide a pressure in response to control signals derived from the controller 32, which in turn is monitoring the output of fluid volume displacement transducer 26. Hydraulic isolation valve 90 may be interposed in the fluid path between fluid port 61 and remote pressurization source 80. In an illustrative embodiment, isolation valve 90 selectively enables fluid communication between fluid port 61 and either pressurization source 80 or an atmospheric vent.

The caisson components listed above represent a subassembly or module embodiment relative to the solvent composition formation subassembly 40 and the pressurization subassembly 80. An advantage to this embodiment, which involves decoupling or modularizing the components as described, is that a plurality of such caissons 14 could be connected to a single solvent composition formation subassembly 40, such that each of n storage matrices 20 could be filled, either concurrently (in parallel, with substantially identical solvent composition), or serially (with the same or with differing solvent composition). Each of these n storage matrices 20 could be connected to a corresponding chromatography column 30. A single pressurization subassembly could be used to pressurize any one of n caissons independently, making use of hydraulic isolation valve 90, or could pressurize all n caissons 14 simultaneously without requiring the use of hydraulic isolation valve 90. In the latter case, the same pressure or pressurization profile would be delivered to all n caissons 14 in an identical manner. The controller 32 via electrical multiplexing as is known in the art, is capable of monitoring volumetric delivery independently at each of the n caissons 14. If an optional pressure sensor 34 is installed in each caisson 14, the controller 32 is also able to monitor pressure independently at each of the n caissons, of use when the independent pressurization mode of operation is selected.

Where the hydraulic isolation valve 90 is employed, an alternating mode of operation is enabled where a first caisson can be usefully engaged in solvent composition expulsion (i.e., performing a chromatographic separation) in response to pressure supplied by the pressure source 80, while a second caisson is engaged with the solvent composition formation subassembly 40 in the storage matrix loading phase of operation in preparation for a next chromatographic separation. Additionally, where hydraulic isolation valve 90 is employed, it is possible for a single pressurization source 80 to pressurize multiple caissons 14 to independent pressures, concurrently. This independent, concurrent operation takes advantage of the fact that the fluidic capacitance of the caisson 14 is typically large relative to the volume of the chromatographic delivery. Therefore, a caisson 14 which has been charged to a particular pressure will remain charged to substantially that pressure for a reasonable period of time, despite the fact that a fluid flow of some nanoliters per minute is being emitted from the storage matrix. Depending upon the magnitude of the fluidic capacitance of the caisson (essentially the magnitude of the energy stored), the pressure source would be required to revisit each caisson 14 at a periodic interval to update its pressure to the required level to achieve the intended volumetric delivery. It will be apparent to one skilled in the art that in any of the multiplecaisson operational modes detailed above, where the output of a single solvent composition formation subassembly 40 is distributed to a plurality of caissons 14, it is also possible to allocate a dedicated solvent formation subassembly 40 to each caisson.

While the illustrative embodiments provided herein refer to a system for high pressure capillary liquid chromatography, it should be understood by one familiar with liquid phase or supercritical fluid phase chemical analysis that the system as described herein could be employed in any area of analysis where a fluid delivery function, incorporating either controlled pressure output, or controlled volumetric delivery output, is desired.

Although the illustrative embodiments described herein comprise the use of a single chromatography column 30, associated with each storage matrix 20, one skilled in the art would appreciate that the system 50 may include alternative numbers of columns 30.

Although the illustrative embodiments described herein comprise the establishment of a solvent composition under substantially atmospheric pressure, it should be appreciated that any selected pressure can be employed for establishing a solvent composition.

While the illustrative embodiments described herein include a storage matrix 20 which is implemented as a single, continuous matrix, it should be appreciated that storage matrix 20 may comprise several or many discrete matrices arranged in fluidic series or in fluidic parallel, or both, and that the several or many discrete matrices may differ in their physical or chemical properties, such as their porosity or their surface chemistry. Further, it should be appreciated that the matrices can be implemented as integrated microfluidic structures.

While the illustrative embodiments described herein include a storage matrix 20 having fluid communication exclusively with fluid accumulator 24 at one end, and with isolation valve 22 and column 30 at the alternate end, it should be appreciated that storage matrix 20, existing either as a single continuous matrix or as multiple discrete, interconnected matrices, may have one or more fluid taps disposed along its length, which allow fluid communication between the storage matrix 20 and points outside the caisson 14. The existence of one or more fluid taps, each having a means to selectively enable or disable fluid flow within the tap, allows for the fluid contents of storage matrix 20 to be shunted into or out of the matrix at one or more defined points. If the material comprising part or all of storage matrix 20 has the ability to adsorb or otherwise temporarily retain analyte species, selective flow shunting can be used to perform sample pre-concentration or sample washing at relatively high flow rate as a part of the solvent composition formation and sample injection process. Alternatively, flow shunting can be used for the purpose of purging the storage matrix 20 with a unidirectional flow of solvent.

While the illustrative embodiment described herein includes an accordion-like bellows which implements the function of fluid accumulator 24, one skilled in the art would appreciate that any of various types of solvent composition 60 containment devices which are displaceable by fluid metering sources may be used.

While the illustrative embodiments described herein incorporate a single storage matrix 20, isolation valve 22, fluid accumulator 24, and fluid volume displacement transducer 26 within a caisson 14, it will be understood that a single caisson 14 could encompass a plurality of storage matrices 20, each with its associated isolation valve 22, fluid accumulator 24, and fluid volume displacement transducer 26, thereby providing a parallel mode of operation where multiple channels of chromatographic separation occur, subject to a common pressure or pressure profile.

It will be understood that various other modifications may be made to the embodiments disclosed herein. For example, the pressurization of fluid 25 within the caisson 14 can be caused by including a plurality of motorized mechanisms (pistons 12 and motors 18), the infiltration of a pressurized gas within caisson 14 or the heating of the fluid 25.

While the embodiments described herein involve formation and expulsion of a solvent composition within storage matrix 20 in a last in—first out compositional order, it should be appreciated that additional valving and fluid taps accessing the storage matrix could be implemented to permit the formation and expulsion of a solvent composition within storage matrix 20 in a first in—first out order.

While the embodiments described herein involve a storage matrix 20 located internal to the pressure caisson 14, thereby enabling the storage matrix 20 to reside at conditions of substantially matched internal and external hydrostatic pressures, it should be appreciated that the storage matrix 20 could be constructed in a manner allowing it to reside outside the pressure caisson. Similarly, isolation valve 22, high-pressure capable injector 28' and chromatographic column 30 may be located internal or external to the pressure caisson as suits the application.

Although the invention has been shown and described with respect to exemplary embodiments thereof, various other changes, omissions and additions in the form and detail thereof may be made therein without departing from the spirit and scope of the invention.

What is claimed is:

1. A high pressure liquid chromatography system establishing a solvent composition at a selected pressure, comprising:

a caisson chamber;

a piston reciprocating in and developing internal pressure of said caisson chamber;

a motor in communication with and driving said piston;

a sensor sensing internal pressure of said caisson;

a solvent composition generator providing a mobile phase to said system;

a storage matrix in fluid communication with said solvent composition generator and receiving said mobile phase; and a fluid accumulator connected by a fluid conduit to said storage matrix, said fluid accumulator being disposed within the interior of said caisson chamber.

2. The system of claim 1 further including a fluid volume displacement sensor detecting volume displacement into said fluid accumulator.

3. The system of claim 2 further including a processor processing information communicated to said processor from said fluid volume displacement sensor, whereby said information is used to calibrate said volume displacement into said fluid accumulator with the volume delivery of solvent from at least one fluid metering unit.

4. The system of claim 2, wherein said fluid volume displacement sensor is selected from the group consisting of: a linear variable differential transformer, capacitance-type transducer, a linear optical encoder, and a resistive transducer.

5. The system of claim 2, wherein said fluid volume displacement sensor produces a signal corresponding to fluid displacement into said fluid accumulator used to calibrate a relationship between displacement of said fluid accumulator and volumetric delivery from said solvent composition generator.

6. The system of claim 5, wherein said fluid volume displacement sensor includes a thick-walled, non-magnetic stainless steel tube interposed between a core and a housing of said fluid volume displacement sensor, such that only said core resides within said caisson chamber.

7. The system of claim 1 further including a valve isolating said solvent composition generator from said caisson chamber.

8. The system of claim 1 further including a seal providing hydraulic sealing between said piston and said caisson chamber.

9. The system of claim 8, wherein said seal resides in a cavity within said caisson chamber and interfaces with an outer diameter of said piston.

10. The system of claim 1, further including an injector in fluid communication with said storage matrix.

11. The system of claim 1, wherein said motor provides rotary motion, and wherein said rotary motion is converted to linear motion by a screw spindle and nut configuration.

12. The system of claim 11, wherein said screw spindle is coupled to said piston by a bearing.

13. The system of claim 1 further including a fill port connected to said caisson chamber to fill said caisson chamber.

14. The system of claim 1, wherein said solvent composition generator further comprises:
   at least one metering unit;
   at least one actuator independently actuating said at least one metering unit; and
   at least one solvent reservoir in fluid connection with said at least one metering unit.

15. The system of claim 14, wherein said at least one metering unit comprises:
   a cylinder;
   a piston disposed within said cylinder;
   a piston seal sealing an interface between said piston and said cylinder; and
   a piston actuator driving said piston.

16. The system of claim 14, wherein said at least one metering unit further comprises a pressure sensor.

17. The system of claim 14, wherein said at least one actuator comprises a step motor.

18. The system of claim 14 further comprising a processor controlling volumetric delivery of fluid from said at least one reservoir.

19. A high pressure liquid chromatography system establishing a solvent composition at a selected pressure, comprising:
   a caisson chamber;
   a means for pressurizing said caisson chamber;
   a fluid composition formation system providing a mobile phase to said system;
   a storage matrix in fluid communication with said fluid composition formation system and receiving said mobile phase; and
   a fluid accumulator connected by a fluid conduit to said storage matrix, said fluid accumulator being disposed within the interior of said caisson chamber.

20. The system of claim 19 further including a sensor sensing internal pressure of said caisson chamber.

21. The system of claim 19 further including a fluid volume displacement sensor detecting fluid displacement into and out of said fluid accumulator.

22. The system of claim 21 further including a processor processing information communicated to said processor from said fluid volume displacement sensor, whereby said information is used to calibrate the fluid displacement into and out of said fluid accumulator with the volume delivery of solvent from at least one fluid metering unit.

23. The system of claim 19 further including a valve isolating said fluid composition formation system from said storage matrix.

24. The system of claim 19 further including a seal providing sealing between said piston and said caisson chamber.

25. The system of claim 19 further including an injector in fluid communication with said storage matrix.

26. The system of claim 25, wherein a sample is injected at low pressure by said injector.

27. The system of claim 25, wherein a sample is injected at high pressure by said injector.

28. The system of claim 19 further including a fill port connected to said caisson chamber to fill said caisson chamber.

29. The system of claim 19, wherein said fluid composition formation system further comprises:
   at least one syringe unit;
   at least one motor independently actuating said at least one syringe unit;
   at least one solvent reservoir in fluid connection with said at least one syringe unit; and
   at least one valve coupling said at least one syringe unit to said at least one solvent reservoir.

30. The system of claim 29, wherein said at least one syringe unit comprises:
   a cylinder;
   a piston disposed within said cylinder;
   a piston seal sealing an interface between said piston and said cylinder; and
   a piston actuator driving said piston.

* * * * *